(12) United States Patent
Lutz et al.

(10) Patent No.: US 8,469,233 B2
(45) Date of Patent: Jun. 25, 2013

(54) DISPENSING DEVICE, KIT CONTAINING THE DEVICE, AND METHOD OF OPERATING THE DEVICE

(75) Inventors: Peter Lutz, Rüdlingen (CH); Annemie Rehor, Winterthur (CH)

(73) Assignee: Kuros Biosurgery AG, Zurich (CH)

( * ) Notice: Subject to any disclaimer, the term of this patent is extended or adjusted under 35 U.S.C. 154(b) by 396 days.

(21) Appl. No.: 12/988,472

(22) PCT Filed: Apr. 16, 2009

(86) PCT No.: PCT/EP2009/054498
§ 371 (c)(1), (2), (4) Date: Oct. 18, 2010

(87) PCT Pub. No.: WO2009/144085
PCT Pub. Date: Dec. 3, 2009

(65) Prior Publication Data
US 2011/0049181 A1    Mar. 3, 2011

(30) Foreign Application Priority Data

Apr. 18, 2008  (CH) ........................................ 0610/08
Jul. 7, 2008   (EP) ..................................... 08104654

(51) Int. Cl.
*B67B 1/00* (2006.01)
(52) U.S. Cl.
USPC ....... 222/1; 222/137; 222/145.6; 222/153.13; 222/386; 604/220
(58) Field of Classification Search
USPC .................. 222/1, 137, 145.1, 145.5, 145.6, 222/153.01, 153.04, 153.13, 326, 327, 386; 604/110, 220
See application file for complete search history.

(56) References Cited

U.S. PATENT DOCUMENTS

| | | | |
|---|---|---|---|
| 3,835,835 | A | 9/1974 | Thompson |
| 4,040,420 | A | 8/1977 | Speer |

(Continued)

FOREIGN PATENT DOCUMENTS

| | | |
|---|---|---|
| DE | 643616 | 4/1937 |
| DE | 1053143 | 3/1959 |

(Continued)

OTHER PUBLICATIONS

Besson, et al., "Synthetic peptide substrates for a conductimetric assay of *Pseudomonas aeruginosa* elastase", Analytical Biochemistry, 237:216-223 (1996).

(Continued)

*Primary Examiner* — Kevin P Shaver
*Assistant Examiner* — Daniel R Shearer
(74) *Attorney, Agent, or Firm* — Pabst Patent Group LLP

(57) ABSTRACT

The application relates to a dispensing device (1) containing at least one chamber (5, 5') for receiving a fluid (B, B'), a plunger unit (6) including at least one piston (7, 7'), locking mechanism and counter-locking mechanism as well as a catching mechanism and counter-catching mechanism. The locking mechanism and the counter-locking mechanism can be brought into a locking position (L), in which a movement of the plunger unit (6) in one or both directions is substantially prevented. The catching mechanism and the counter-catching mechanism can be brought into an engagement position (E), in which the locking mechanism and the counter-locking mechanism cannot be brought into the locking position (L). Furthermore, the application relates to a kit (19) containing the dispensing device (1) and to a method of operating the device (1) or kit (19).

13 Claims, 12 Drawing Sheets

U.S. PATENT DOCUMENTS

| | | | |
|---|---|---|---|
| 4,552,155 A * | 11/1985 | Etherington et al. | 600/579 |
| 4,758,232 A * | 7/1988 | Chak | 604/220 |
| 4,978,336 A | 12/1990 | Capozzi | |
| 4,979,942 A | 12/1990 | Wolf | |
| 5,104,375 A | 4/1992 | Wolf | |
| 5,116,315 A | 5/1992 | Capozzi | |
| 5,215,536 A * | 6/1993 | Lampropoulos et al. | 604/220 |
| 5,249,862 A | 10/1993 | Herold | |
| 5,468,232 A * | 11/1995 | Naganuma | 604/200 |
| 5,605,255 A | 2/1997 | Reidel | |
| 5,651,372 A * | 7/1997 | Caillouette | 600/567 |
| 5,664,733 A | 9/1997 | Lott | |
| 5,688,250 A * | 11/1997 | Naganuma | 604/200 |
| 5,924,600 A | 7/1999 | Keller | |
| 5,968,018 A | 10/1999 | Freeman | |
| 5,997,811 A | 12/1999 | Esposito | |
| 6,123,687 A | 9/2000 | Simonyi | |
| 6,135,631 A | 10/2000 | Keller | |
| 6,244,740 B1 | 6/2001 | Wagner | |
| 6,328,299 B1 | 12/2001 | Coombs | |
| 6,331,422 B1 | 12/2001 | Hubbell | |
| 6,371,941 B1 * | 4/2002 | Kato et al. | 604/220 |
| 6,458,095 B1 | 10/2002 | Wirt | |
| 6,475,183 B1 | 11/2002 | Epstein | |
| 6,488,650 B1 | 12/2002 | Epstein | |
| 6,569,113 B2 | 5/2003 | Wirt | |
| 6,575,205 B2 | 6/2003 | Epstein | |
| 6,582,407 B1 | 6/2003 | Lo | |
| 6,610,033 B1 | 8/2003 | Melanson | |
| 6,648,852 B2 | 11/2003 | Wirt | |
| 6,789,750 B1 | 9/2004 | Heldt | |
| 6,796,969 B1 * | 9/2004 | Andersson | 604/198 |
| 7,077,339 B2 | 7/2006 | Leach | |
| 7,081,103 B2 | 7/2006 | Epstein | |
| 7,207,969 B2 | 4/2007 | Epstein | |
| 7,247,609 B2 | 7/2007 | Lutolf | |
| 7,316,330 B2 | 1/2008 | Muller | |
| 7,320,541 B2 | 1/2008 | Wagner | |
| 7,470,260 B2 | 12/2008 | Gurtner | |
| 7,699,813 B2 | 4/2010 | Liversidge | |
| 7,736,049 B2 | 6/2010 | Keller | |
| 7,954,672 B2 | 6/2011 | Keller | |
| 2002/0072714 A1 | 6/2002 | Epstein | |
| 2002/0198490 A1 | 12/2002 | Wirt | |
| 2003/0083606 A1 | 5/2003 | Epstein | |
| 2003/0139774 A1 | 7/2003 | Epstein | |
| 2003/0187387 A1 | 10/2003 | Wirt | |
| 2003/0209612 A1 | 11/2003 | Hahnen | |
| 2004/0159715 A1 | 8/2004 | Leach | |
| 2005/0154362 A1 | 7/2005 | Warren | |
| 2005/0226095 A1 | 10/2005 | Wagner | |
| 2005/0230422 A1 | 10/2005 | Muller | |
| 2005/0277893 A1 | 12/2005 | Liversidge | |
| 2006/0227653 A1 | 10/2006 | Keller | |
| 2007/0010440 A1 | 1/2007 | Schense | |
| 2007/0265579 A1 | 11/2007 | Kleyman | |
| 2007/0275028 A1 | 11/2007 | Barry | |
| 2007/0276505 A1 | 11/2007 | Barry | |
| 2008/0029542 A1 | 2/2008 | Keller | |
| 2008/0093392 A1 | 4/2008 | Abduljalil | |
| 2008/0128454 A1 | 6/2008 | Beckett | |
| 2008/0267005 A1 | 10/2008 | Reinprecht | |
| 2008/0287880 A1 | 11/2008 | Keller | |
| 2009/0020561 A1 | 1/2009 | Keller | |
| 2009/0062745 A1 * | 3/2009 | Qiu | 604/197 |
| 2009/0134186 A1 | 5/2009 | Keller | |
| 2009/0198195 A1 | 8/2009 | Gurtner | |
| 2009/0204076 A1 | 8/2009 | Liversidge | |
| 2010/0063474 A1 | 3/2010 | Evans | |
| 2010/0102088 A1 | 4/2010 | Keller | |
| 2010/0106085 A1 | 4/2010 | Perot | |
| 2010/0106138 A1 | 4/2010 | Chavarria | |
| 2010/0114158 A1 | 5/2010 | Hattan | |
| 2010/0121268 A1 | 5/2010 | Keller | |
| 2010/0160869 A1 | 6/2010 | Liversidge | |
| 2010/0204670 A1 | 8/2010 | Kraushaar | |
| 2010/0204671 A1 | 8/2010 | Kraushaar | |
| 2010/0260004 A1 | 10/2010 | Wang | |
| 2011/0009815 A1 | 1/2011 | Stormer-Talleur | |
| 2011/0098657 A1 | 4/2011 | Jennings | |
| 2011/0139821 A1 | 6/2011 | Greter | |

FOREIGN PATENT DOCUMENTS

| | | |
|---|---|---|
| DE | 202006004738 | 6/2006 |
| DE | 202006005663 | 6/2006 |
| EP | 0420126 | 4/1991 |
| EP | 0550767 | 7/1993 |
| EP | 0634140 | 1/1995 |
| EP | 0911046 | 4/1999 |
| EP | 1172154 | 1/2002 |
| JP | 8229122 | 9/1996 |
| WO | 03052091 | 6/2003 |
| WO | 2006072622 | 7/2006 |
| WO | 2006072623 | 7/2006 |
| WO | 2007131371 | 11/2007 |
| WO | 2007137653 | 12/2007 |
| WO | 2008131154 | 10/2008 |
| WO | 2008148539 | 12/2008 |
| WO | 2010145041 | 12/2010 |

OTHER PUBLICATIONS

Coombs, et al., "Directing sequence-specific proteolysis to new targets. The influence of loop size and target sequence on selective proteolysis by tissue-type plasminogen activator and urokinase-type plasminogen activator", J. Biol. Chem., 273:4323-4328 (1998).

Gabriel, et al., "The Effect of Fibrin Structure on Fibrinolysis", J. of Biological Chemistry, 267(34):24259-24263 (1992).

Jones & Goodall, "Differential effects of the iodinated contrast agents Ioxaglate, Iohexol and Iodixanol on thrombus formation and fibrinolysis", Thrombosis Research, 112(1-2):65-71 (2003).

Netzel-Arnett, et al., "Sequence specificities of human fibroblast and neutrophil collagenases", J. Biol. Chem., 266:6747-6755 (1991).

Predey, et al., "Percutaneous vertebroplasty: new treatment for vertebral compression fractures", American Family Physician, 66(4):611-615 (2002).

Smith, et al., "Rapid identification of highly active and selective substrates for stromelysin and matrilysin using bacteriophage peptide display libraries", J. Biol. Chem., 270:6440-6449 (1995).

Takagi & Doolittle, "Amino acid sequence studies on the alpha chain of human fibrinogen. Location of four plasmin attack points and a covalent cross-linking site", Biochem., 14:5149-5156 (1975).

Trout, et al. "New fractures after vertebroplasty: adjacent fractures occur significantly sooner", Journal of Neuroradiology, 27(1):217-23 (2006).

* cited by examiner

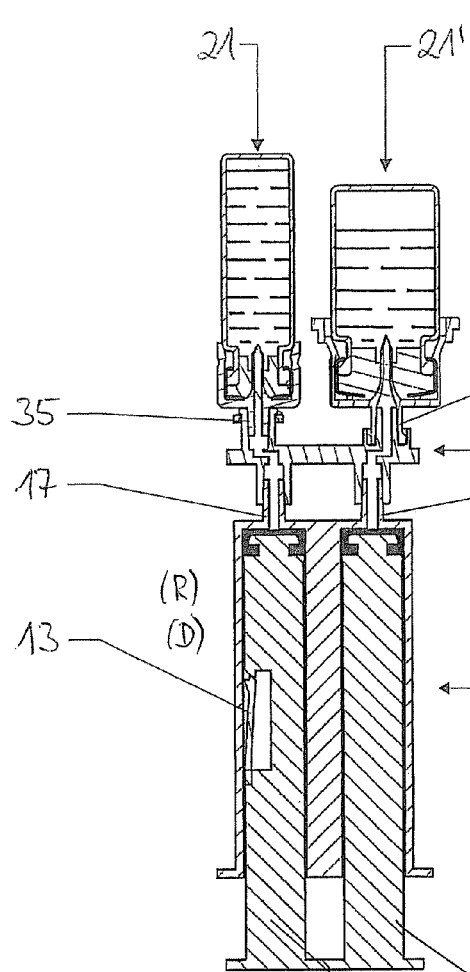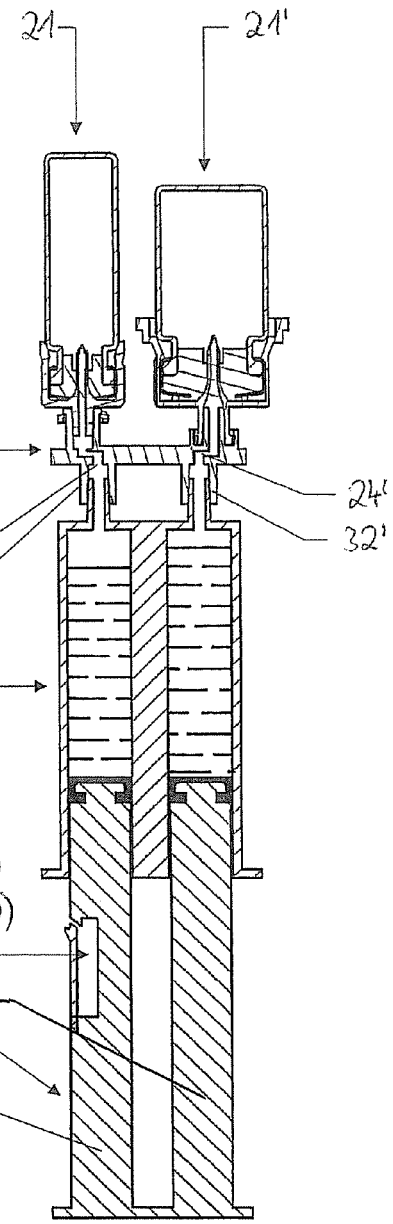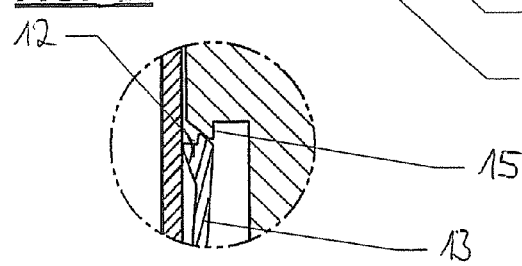

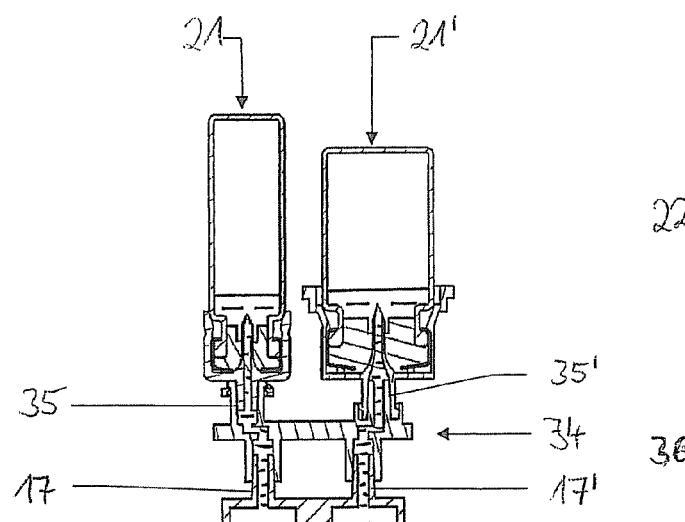
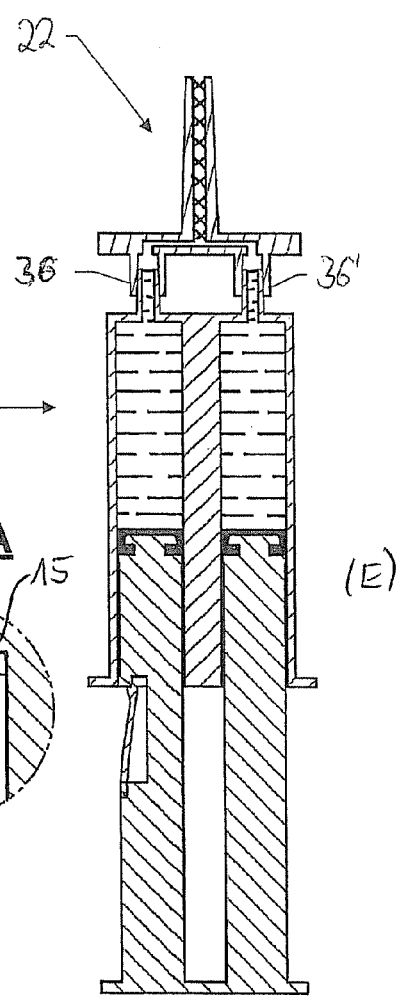
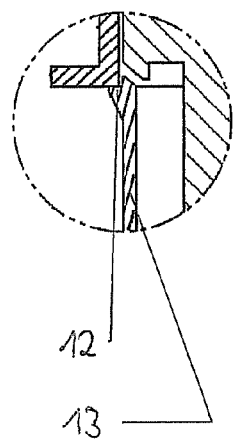
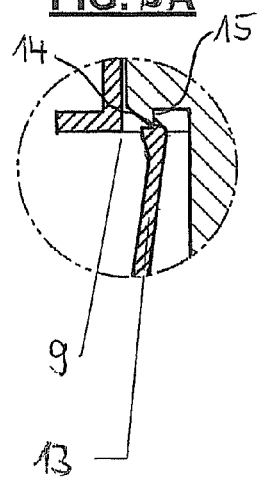

DISPENSING DEVICE, KIT CONTAINING THE DEVICE, AND METHOD OF OPERATING THE DEVICE

This application is a filing under 35 U.S.C. §371 of PCT/EP2009/054498 filed with the European Receiving Office of the Patent Cooperation Treaty on Apr. 16, 2009, which claims the benefit under 35 U.S.C. §119 of Swiss application number CH 00610/08, filed Apr. 18, 2009 and European application number EP08104654.2 filed Jul. 7, 2008.

The present invention relates to a dispensing device, a kit containing the device, and a method of operating the device. Such a device may be used for receiving, storing, and ejecting at least one fluid, in particular several fluids. In some embodiments, the device may be used for ejecting several fluids to be mixed directly upon ejection.

A comparable dispensing device in the form of a syringe is shown in DE 1 053 143. This device has a main body with a front end, an opposite rear end, and a chamber between the front end and the rear end for receiving a fluid. Furthermore, the device contains a plunger comprising a piston, which is arranged slidingly in the chamber.

The chamber can be filled with an injection fluid by directly or indirectly connecting it with a fluid reservoir and retracting the plunger. The plunger contains several locking teeth which can be locked relative to the main body with the help of a locking lever. With these locking means and counter-locking means, a locking position may be obtained, in which a movement of the plunger in the direction from the rear end to the front end is prevented, thereby also preventing the ejection of the fluid. In order to release this locking, the locking lever is activated, which releases the plunger again and thereby allows the ejection of the fluid.

However, the device disclosed in this document has several disadvantages. Inter alia, the operation of this device is rather complicated. In particular, the locking lever has to be activated for the entire period of time during which the plunger is to be moved.

Moreover, EP 420 126 discloses a blood sample removal device comprising locking teeth which are engageable with a resilient locking stop, which prevents a movement of the piston in one direction. However, the engagement of the locking teeth and the locking stop cannot be reversed during a proper operation of the device. Consequently, the plunger cannot be re-inserted into the chamber, thereby preventing a re-ejection of the fluid through the inlet opening.

It is therefore an object of the present invention to provide a dispensing device which overcomes the drawbacks of the prior art, which in particular allows for an easy operation.

This goal is achieved by a dispensing device containing at least one chamber, a plunger unit, locking means, and counter locking means, wherein, according to the invention, the device further comprises catching means and counter-catching means.

The dispensing device may contain only a single chamber such as the device described in DE 1 053 143. However, preferably, the device is a multi-chamber dispensing device or, more preferably, a two-chamber dispensing device. Such a two-chambered dispensing device is known, for example, from WO 2007/131371.

The dispensing device contains a main body comprising a front end and an opposite rear end. Between the front end and the rear end, there is arranged at least one chamber for receiving a fluid. Each of the chambers comprises an opening at the front end of the main body, which serves as a fluid inlet and/or outlet. The fluid may be a gas. However, preferably, the fluid to be received is a liquid. The viscosity of the liquid can vary over a wide range, i. e. from paste-like to liquid.

The plunger unit comprises at least one piston, wherein each piston is arranged slidingly in one of the chambers. Preferably, the pistons are rigidly connected to each other.

The locking means and the counter-locking means can be brought into a locking position. In the locking position, a movement of the plunger unit in one or both directions is substantially prevented. Thereby, a relative fixation of the plunger unit with respect to the main body is achieved, so that the injection of a fluid into the chamber or chambers and/or the ejection of a fluid out of the chamber or chambers is prevented. Such a fixation can be desirable when at least one of the chambers is subjected to an over-pressure or an under-pressure.

According to the invention, the catching means and the counter-catching means can be brought into an engagement position, in which the locking means and the counter-locking means cannot be brought into the locking position.

Therefore, when the catching means and the counter-catching means are in the engagement position, the engagement of the catching means and the counter-catching means releases the locking induced by the locking means and the counter-locking means. Thus, in the engagement position, the relative movement of the plunger unit with respect to the main body is not restricted in one or both directions. Consequently, the relative movability of the plunger unit with respect to the main body can be controlled by the position of the catching means and the counter-catching means.

In some embodiments, the device may contain several locking means and/or corresponding counter-locking means, wherein different combinations of locking means and counter-locking means define different locking positions. Thus, the device may be selectively brought into one of the locking positions, which may define different relative positions of the plunger unit and the main body.

Preferably, the locking means and the counter-locking means can not only be brought into a locking position, but also into a releasing position. In this releasing position, a movement of the plunger unit is possible in both directions. Even more preferably, the catching means and the counter-catching means can be designed such that when they are in the engagement position, the locking means and the counter-locking means can be brought into the releasing position.

Therefore, when the catching means and the counter-catching means are in the engagement position, the plunger unit can be moved in both directions, which allows both an injection and an ejection of fluids by a respective movement of the plunger.

Preferably, the catching means and the counter-catching means may not only obtain an engagement position, but also a disengagement position in which the locking means and the counter-locking means can be brought into the locking position.

Consequently, when the catching means and the counter-catching means are in the disengagement position, the locking position may be obtained, in which the movement of the plunger unit in one or both directions is substantially prevented. Thus, the injection and/or the ejection of fluids are prevented.

In a preferred embodiment, in the locking position, a movement of the plunger unit in the direction from the rear end to the front end is prevented. Thus, when this locking position is obtained, a movement of the plunger is prevented when at least one of the chambers is subject to an under-pressure so that the ejection of a fluid or fluids out of the chambers is prevented. Such an under-pressure in a chamber can occur when fluids are inserted from a fluid reservoir having under-pressure.

Preferably, the catching means are different from the locking means and/or the counter-catching means are different from the counter-locking means. Thus, the mechanisms provided by the locking means and the counter-locking means on the one hand and by the catching means and the counter-catching means on the other hand may be different from one another.

In summary, the relative position of the catching means and the counter-catching means determines whether the locking means and the counter-locking means can be brought into the locking position or not, i. e. whether the movement of the plunger unit can be prevented in one direction or not. Therefore, when the catching means and the counter-catching means are in the engagement position, the plunger unit cannot be locked relative to the main body of the device unintentionally, which facilitates the injection and/or ejection of the fluid or fluids.

In a preferred embodiment, the device may contain stopping means which are arranged such that a movement of the plunger unit is limited in the direction from the front end to the rear end of the device. In any case, the stopping means do not prevent the achievement of the locking position. Therefore, the plunger unit may be retracted from the main body to such an extent that the locking position is obtained. Preferably, the stopping means prevent the complete removal of the plunger unit from the main body of the device.

According to a preferred embodiment, the stopping means are arranged such that when the locking means and the counter-locking means are in the locking position, the plunger unit is still movable in the direction from the front end to the rear end by a pre-defined distance.

Due to this construction, a fluid or fluids may be inserted from a fluid reservoir or fluid reservoirs into the chamber or chambers of the device by retracting the plunger unit until the locking position is obtained. From this locking position, the plunger unit can be further retracted from the main body by the pre-defined distance, whereby an excess of fluid or fluids is temporarily inserted into the chamber or chambers. This ensures that the openings of the device and, possibly, ducts of a connecting adapter connecting the openings and the reservoirs are completely flooded with the fluids. The plunger unit is then released again, so that it moves back to the locking position due to the under-pressure.

Preferably, the stopping means contain a first stopping surface and a second stopping surface. In one embodiment, the first stopping surface is arranged on the plunger unit, whereas the second stopping surface is arranged on the main body, in particular on the inside of one of the chambers of the device.

According to a preferred embodiment, the locking means and the counter-locking means are arranged in such a way that in the disengagement position, the following two states may be obtained: In the releasing position, the locking means and/or the counter-locking means are resiliently supported by a tensioned supporting element, in particular radially. In the locking position, the supporting element is less tensioned.

Thus, in the disengagement position, the locking position may be obtained from the releasing position by a release of tension of the supporting element, wherein this release of tension may occur automatically during retraction of the plunger unit. By this release, the locking means and/or the counter-locking means can move automatically, in particular radially, so that the locking position is obtained.

Preferably, the locking means comprise at least one radial protrusion, in particular at least one radially extending tooth. In one embodiment, the protrusion, in particular the tooth, is engageable with counter-locking means arranged on the main body of the device.

According to one embodiment, the plunger unit contains the catching means and the counter-catching means. However, it is also conceivable that the main body of the device contains the catching means and/or the counter-catching means.

In a preferred embodiment, the plunger unit comprises the supporting element. The supporting element may be designed as at least one retaining arm. With preference, the retaining arm is flexible and bendable in a radial direction, in particular in a radial direction. The retaining arm may further contain a tip forming the catching means and a retaining surface forming the counter-catching means. Preferably, the plunger unit, in particular the retaining arm, contains the locking means, as for example a tooth, which may be extending radially outwardly.

In one embodiment, the retaining arm extends in a longitudinal axis of the device and is fixed to a main portion of the plunger unit at one of its ends which points in the direction of the rear end of the device. In this embodiment, the tip points in the direction of the front end.

Preferably, the catching means and the counter-catching means can be brought from the disengagement position into the engagement position by exerting an inward radial force on the plunger unit, in particular on the retaining arm. When the engagement position is obtained, the catching means and the counter-catching means remain in this position even when the force is removed, which simplifies the operation of the device significantly.

In one embodiment, a cavity is formed radially between the retaining arm and a main portion of the plunger unit. This cavity can receive the retaining arm in a bent position.

In certain embodiments, the retaining arm may lose its tension due to a fatigue of material when it has been maintained in a bent position over a certain time, for example during storage of the device. Therefore, the cavity between the retaining arm and the main portion of the plunger unit may be partly or completely filled with an additional elastic supporting element. The additional elastic supporting element can maintain an additional tension and provide an additional radial support of the retaining arm and the protrusion.

In some embodiments, the device may contain two or more retaining arms, each one containing at least one radially extending tooth serving as locking means. Thus, each retaining arm corresponds to a different locking position defining different relative positions of the plunger unit and the main body.

In a further alternative, instead of a retaining arm, a metal spring member can be clipped into a corresponding receptacle of the plunger unit.

During filling the device with one or more fluids from one or more fluid reservoirs, air may be unintentionally entrapped in the one or more chamber of the device. This may occur, for example, when the fluids are injected via an adapter having ducts which are initially filled with air. In order to eject this unintentionally entrapped air, the device is usually held in an at least approximately vertical position, and the plunger unit is at least partially re-inserted into the chambers until the air has left the chambers through the openings.

However, when the device is not held exactly vertical, the air entrapments in only some of the chambers are removed, or only parts of the air entrapments are removed. In those chambers in which, due to the tilting of the device, the air entrapment is not adjacent to the opening in this chamber, only fluid is ejected, but not the air. This problem may occur, for example, with the device shown in WO 2007/131371.

The document U.S. Pat. No. 4,040,420 discloses a two-chamber device comprising a tapered nozzle and an off-set conical transition section joining the nozzle to the chambers. A similar device is disclosed in DE 20 2006 005 663. The shapes of the chambers shown in these two documents facilitate the removal of air entrapments occurring during an unintentional tilting. However, the devices shown there are disadvantageous since the chambers cannot be completely emptied, which means a waste of fluid. Moreover, already before filling the chambers with the fluids, there are air entrapments in these chambers.

Therefore, according to another and independent aspect of the present invention, a tip surface of at least one piston is essentially complementary to an end surface of the respective chamber which contains the opening. Consequently, prior to injecting the fluids into the chambers, when the pistons are completely inserted, there are essentially no air entrapments in the chambers. Furthermore, during re-ejection of the fluids by re-inserting the pistons, essentially no fluids can remain in the chambers.

According to the invention, at least one of the chambers, in particular the end surface of at least one of the chambers, is designed such that its cross-sections is reduced in the direction of a respective opening, i. e. in the direction of the front end. The device exhibits an (imaginary) tilting axis which is perpendicular to a longitudinal axis of the device. The longitudinal axis of the device may be tilted from the vertical direction about this tilting axis in two opposed (rotational) tilting directions. According to the invention, the device exhibits a critical tilting angle such that the following property is satisfied for a tilting in at least one of the two tilting directions: When the device is tilted by a tilting angle not exceeding a critical tilting angle, all chambers have essentially no dead volume. A chamber has "no dead volume" for a specific tilting angle when no air entrapment can be formed which is not adjacent to the opening in the end surface. In other words, when the chamber has no dead volume for a specific tilting angle, all possible air entrapments are situated adjacent to this opening and can therefore be removed by moving the piston arranged in this chamber.

However, when the tilting angle exceeds the critical tilting angle and is maintained during the ejection of the fluid, the air entrapment in the chamber can only escape through the opening when the piston is completely inserted into the chamber, i. e. when its tip surface contacts the end surface of the chamber. Therefore, the entrapped air can only escape when the entire fluid has already been ejected through the opening.

In preferred embodiments, the critical tilting angle is at least 10°, more preferably at least 15°, even more preferably at least 20°, most preferably about 25°.

Furthermore, according to the invention, the openings are arranged adjacent to one another. Particularly, the openings may have a distance from each other which is smaller than one-half of the sum of the inner dimensions of the chambers in a plane perpendicular to their longitudinal axis. This embodiment allows the ejection of fluids from nearby positions and can therefore facilitate an optional subsequent mixing of the fluids, thereby diminishing the necessary size of a mixing assembly to be used.

In one embodiment, the end surface of at least one chamber is essentially planar. Preferably, the end surfaces of all chambers are essentially planar. At least one of the planar end surfaces is inclined by an angle with respect to a plane which is perpendicular to a longitudinal axis of the device. The surfaces are inclined such that when the device is in an upright position, the opening is adjacent to the topmost portion of the surface. Here, the device is in an upright position when its longitudinal axis is vertical and the front end is directed upwards. Preferably, this angle is at least 10°, more preferably at least 15°, even more preferably at least 20°, most preferably about 25°. In these embodiments, this angle corresponds to the critical tilting angle of the device.

It is conceivable that the device exhibits several tilting directions, such that for any tilting angle in any of these tilting directions, which does exceed the critical tilting angle, all chambers have essentially no dead volume. For example, the device may be tiltable about a tilting axis in both opposite tilting directions.

A further aspect of the invention is directed to a multiple connecting adapter, in particular a double connecting adapter. Such a multiple connecting adapter can be used for indirectly connecting each of at least two openings of a multi-chamber dispensing device with a respective fluid reservoir simultaneously. Moreover, it can be used for simultaneously transferring fluids contained in the fluid reservoirs to respective chambers of the device via the openings. The multi-chamber dispensing device may have some or all of the properties described above.

According to the invention, the multiple connecting adapter comprises at least two ducts. A first end of each duct opens out into a respective device-facing opening, which is connectable or connected with a respective opening of the device. Furthermore, a second end of each duct, which is opposite to the respective first end of the duct, opens out into a respective reservoir-facing opening, which is connectable or connected with a respective fluid reservoir.

Preferably, the first ends of ducts of the adapter are adapted to the openings of the device. In some embodiments, the first ends of the ducts are conical, and also the openings of the device are conical. This facilitates the connection of the adapter and the device.

In some embodiments, the second ends of the ducts of the adapter are male or female Luer lock connectors. In certain embodiments, one second end may be a male Luer lock connector, and another second end may be a female Luer lock connector.

In some embodiments, the first ends may be identical. In other embodiments, they may be different from one another.

Moreover, at least one of the first ends and/or at least one of the second ends of the adapter may be coded connectors. For example, they may be visually or geometrically coded in order to avoid a confusion of the connectors. For the same purpose, also the openings of the dispensing device and/or the reservoir connectors may be coded.

A further aspect of the invention is concerned with a kit containing a device according to the present invention as well as at least one of the following components:

The kit may contain a multiple connecting adapter, in particular a multiple connecting adapter as described above.

Furthermore, the kit may contain a mixing assembly for mixing fluids ejected from the chambers. Additionally, the kit may contain a spray assembly for spraying fluids to be ejected from the chambers. Such mixing assemblies and spray assemblies are described, by way of example, in WO 2007/131371.

A further aspect of the invention relates to a method of operating a device or a kit containing the device according to the invention. The method comprises the following steps:
   i) providing at least one fluid reservoir, at least one of the fluid reservoirs containing a fluid;

ii) directly or indirectly connecting openings of each chamber of the device with a respective fluid reservoir, in particular by a multiple connecting adapter;
iii) at least partially retracting the piston or pistons of the device from the chamber or chambers;
iv) allowing the locking means and the counter-locking means to obtain the locking position;
v) disconnecting the openings from the respective fluid reservoirs;
vi) bringing the catching means and the counter-catching means into the disengagement position, in particular by a one-hand operation;
vii) at least partially inserting the pistons into the chambers, thereby ejecting the fluids, in particular through a mixing assembly and/or a spray assembly.

Preferably, prior to step i), the device is provided in a state in which the pistons are essentially completely inserted in the chambers. Alternatively, the device may be brought into this state.

Preferably, between steps iv) and v), the piston or pistons is/are further retracted, in particular until the stopping means are in a position in which the plunger unit is not further retractable in the direction from the front end to the rear end of the dispensing device, and the piston or pistons is/are then reinserted, in particular until the tooth and the rear surface are in contact. By performing these optional, additional steps, the amount of fluids contained in the chamber or chambers can be adjusted, and possible air entrapments can be removed from the chamber or chambers.

The dispensing device according to the invention may also be used in methods differing from the one described above. For example, when one chamber of the dispensing device is already filled, another chamber may be filled with the aid of a single connecting adapter containing only one duct with two openings. Moreover, in order to suck in a liquid, such as blood, a needle may be connected to one of the openings of the dispensing device, for example with the aid of a Luer connector. In these methods, in which only one of the chambers is filled from a reservoir, the plunger unit has to contain two pistons which are separately movable but connectable to be movable together.

The invention will now be explained in more detail by non-limiting examples and figures, wherein FIG. 1 shows a first dispensing device according to the present invention in the simultaneous releasing position and disengagement position;

FIG. 10 shows the second kit of FIG. 8 wherein the second dispensing device is in a simultaneous releasing position and disengagement position;

FIG. 10A show a detailed view of the tip of a retaining arm depicted in FIG. 10;

FIG. 11 shows the second kit of FIG. 8 wherein the second dispensing device is in a simultaneous locking position and disengagement position and wherein a tooth of the retaining arm is not in contact with a rear surface of the device;

FIG. 12 shows the second kit of FIG. 8 wherein the second dispensing device is in the simultaneous locking position and disengagement position and wherein the tooth of the retaining arm not in contact with the rear surface of the device;

FIG. 12A show a detailed view of the tip of a retaining arm depicted in FIG. 12;

FIG. 13 shows the second dispensing device of FIG. 8 and a mixing device, wherein the dispensing device is in the simultaneous engagement position and releasing position;

FIG. 13A show a detailed view of the tip of a retaining arm depicted in FIG. 13;

Figure 1:
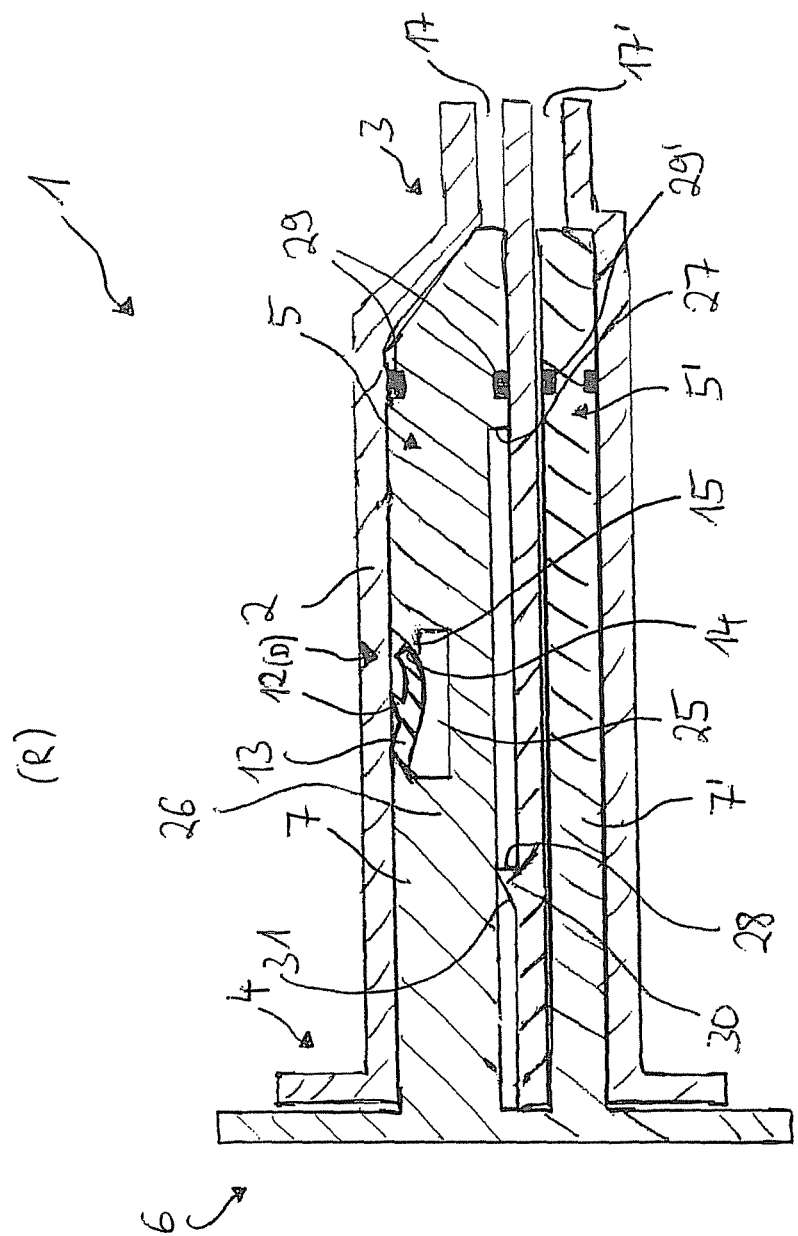

The dispensing device 1 depicted in FIGS. 1 through 4 has a main body 2 comprising a front end 3 and an opposite rear end 4. The main body 2 comprises two chambers 5,5' between the front end 3 and the rear end 4 for receiving a fluid. The chambers 5,5' have a length of 85 mm. Both chambers 5,5' have a circular cross section, wherein the cross section of the first chamber 5 is larger than the cross section of the second chamber 5'. The ratio of the cross section may be, for example, 1:1, 4:1 or 10:1. In particular, the cross sections may be 10/11 cm$^2$ and 1/11 cm$^2$. It is to be noted that the figures are not drawn to scale. Each of the chambers 5,5' has an opening 17,17' at the front end 3, which serves as a fluid inlet and/or outlet. The device 1 further comprises a plunger unit 6 comprising two pistons 7,7', each of which is arranged slidingly in one of the chambers 5,5'. Both pistons 7,7' are rigidly connected to each other. In particular, the entire plunger unit 6 including the pistons 7,7' may be an integral part. Each of the pistons 7,7' carries a respective o-ring 29,29', which serve to seal the chambers 5,5'.

The plunger unit 6 comprises a retaining arm 13, which extends in the longitudinal axis of the device 1 and is fixed to a main portion 26 of the plunger unit 6 at its end pointing in the direction of the rear end 4. The retaining arm 13 contains a tip 14 pointing in the direction of the front end 3. The tip 14 forms catching means according to the invention. Radially between the retaining arm 13 and the main portion 26 of the plunger unit 6, a cavity 25 is formed. Furthermore, the plunger unit 6 comprises a retaining surface 15, which forms counter-catching means. Additionally, the retaining arm 13 contains a protrusion in the form of a radially extending tooth 12, which forms locking means according to the invention.

Moreover, the plunger unit 6 contains a first stopping surface 27, and the first chamber 5 contains a second stopping surface 28. The first stopping surface 27 is formed as a portion of the surface of a cam 30. The opposite surface 31 of the cam 30 is chamfered in order to allow the assembly of the device 1. The first stopping surface 27 and the second stopping surface 28 form stopping means which limit the movement of the plunger unit 6 in the direction from the front end 3 to the rear end 4 of the device 1. In particular, the first stopping surface 27 and the second stopping surface 28 are arranged such as to prevent the complete removal of the plunger unit 6 from the main body 2 of the device 1. It is obvious that the device 1 may contain more than one cam 30 containing first stopping surfaces 27. Moreover, the cam or cams 30 may be arranged at any angle around the longitudinal axis A of the device 1. In particular, at least one of the cams 30 may be arranged outside the plane defined by the longitudinal axis A and the retaining arm 13, i. e. outside the drawing plane in FIGS. 1 to 4.

The main body 2 and/or the plunger unit 6 comprising the pistons 7,7' are composed of or contain a plastic material. They can be manufactured, for example, by injection molding. In one embodiment, the plunger unit 6 containing the pistons 7,7' and the retaining arm 14 may be injection-molded as an integral part. In a particular embodiment, the plunger unit 6 may be made from a fiber-glass reinforced plastic material.

Figure 2:
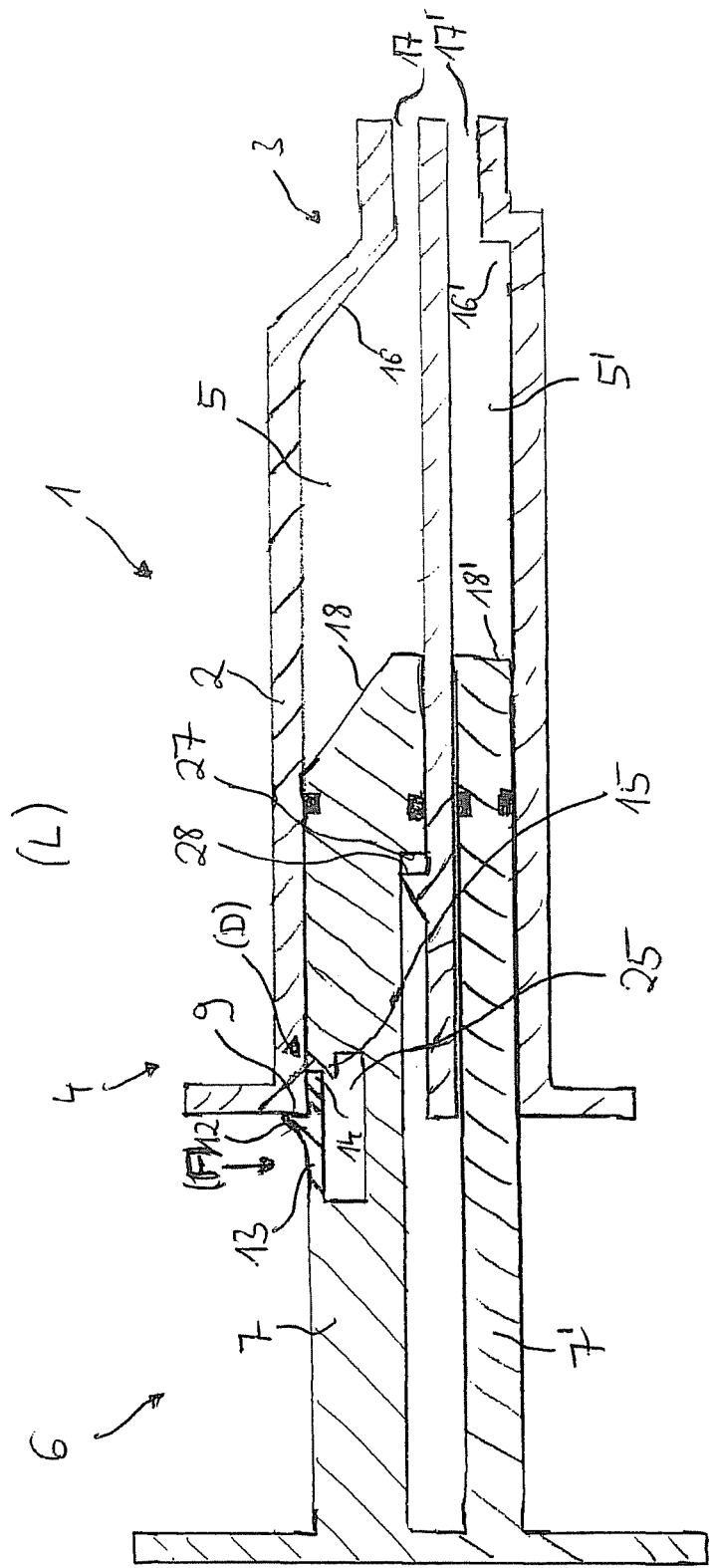
FIG. 2 shows the dispensing device of FIG. 1 in the simultaneous locking position and disengagement position.

In the state shown in FIG. 1, the tip 14 of the retaining arm 13 is situated on the radially outwardly directed side of the retaining surface 15. Hence, the tooth 12 arranged on the retaining arm 13 is in contact with the inner surface of the first chamber 5. Due to the contact of the tooth 12 with the inner wall of the first chamber 5, the retaining arm 13 is bent. Accordingly, the tooth 12 is resiliently radially supported against the inner surface of the first chamber 5. The tip 14 and the retaining surface 15 are in a disengagement position D, which allows a locking position (cp. FIG. 2 and the corresponding description below). However, the contact between the tooth 12 and the inner surface of the first chamber 5 does not significantly prevent the movement of the plunger unit 6 in both directions, so that, in FIG. 1, the releasing position R is present.

When the plunger unit 6 is retracted from the main body 2 to a certain extent, the tooth 12 snaps behind a rear surface 9 of the main body 2, whereby the rear surface 9 forms counter-locking means. The outward radial movement of the tooth 12 is automatically initiated by a release of tension of the retaining arm 13. Thus, the retaining arm 13 functions as supporting element. In the state shown in FIG. 2, the tooth 12 and the rear surface 9 are engaged in a locking position L, in which a movement of the plunger unit 6 in the direction from the rear end 4 to the front end 3 is prevented. Thus, even when an under-pressure is present in one of the chambers 5,5', the pistons 7,7' cannot be pulled back into the chambers 5,5'. As can be seen from FIG. 2, the arrangement of the first stopping surface 27 and the second stopping surface 28 do not prevent the achievement of the locking position L.

In certain embodiments, the retaining arm 13 may lose its tension due to a fatigue of material when it has been maintained in the bent position as shown in FIG. 1. This fatigue may prevent the movement to the locking position L shown in FIG. 2. Therefore, the cavity 25 may be partly or completely filled with an additional elastic supporting element, which is not shown in the drawings. The additional elastic supporting element can maintain an additional tension, thereby eliminating the above-mentioned problem of fatigue. Preferably, the additional elastic supporting element is an elastic pad, such as a silicone pad, or a spring.

The disengagement position D of the tip 14 and the retaining surface 15 is still maintained, even when the locking position L is obtained as in FIG. 2.

Figure 3:
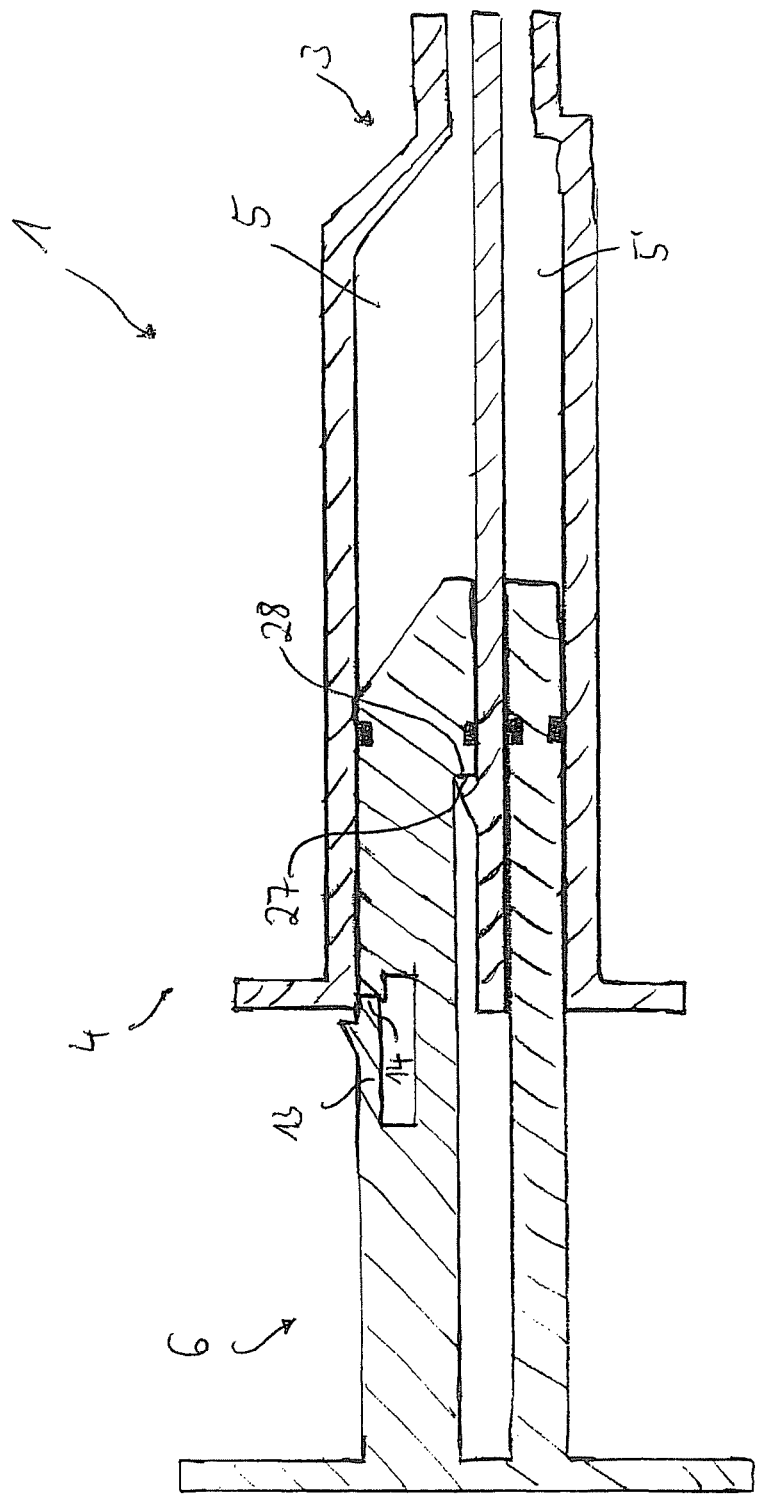
FIG. 3 shows the dispensing device of FIG. 1 in the simultaneous locking position and disengagement position, wherein the first stopping surface and the second stopping surface are in contact.

From the locking position (L) according to FIG. 2, the plunger unit 6 can be further moved in the direction from the front end 3 to the rear end 4 until the first stopping surface 27 and the second stopping surface 28 are in contact, so that the position shown in FIG. 3 is obtained. The arrangement of the first stopping surface 27 and the second stopping surface 28 determines the distance by which the plunger unit 6 is further retractable.

Furthermore, the retaining arm 13 is dimensioned and arranged relative to the first stopping surface 27 and the second stopping surface 28 such that its tip 14 does not leave the first chamber 5, which facilitates the insertion of the plunger unit 6 to be performed in a later step (see below).

Figure 4:
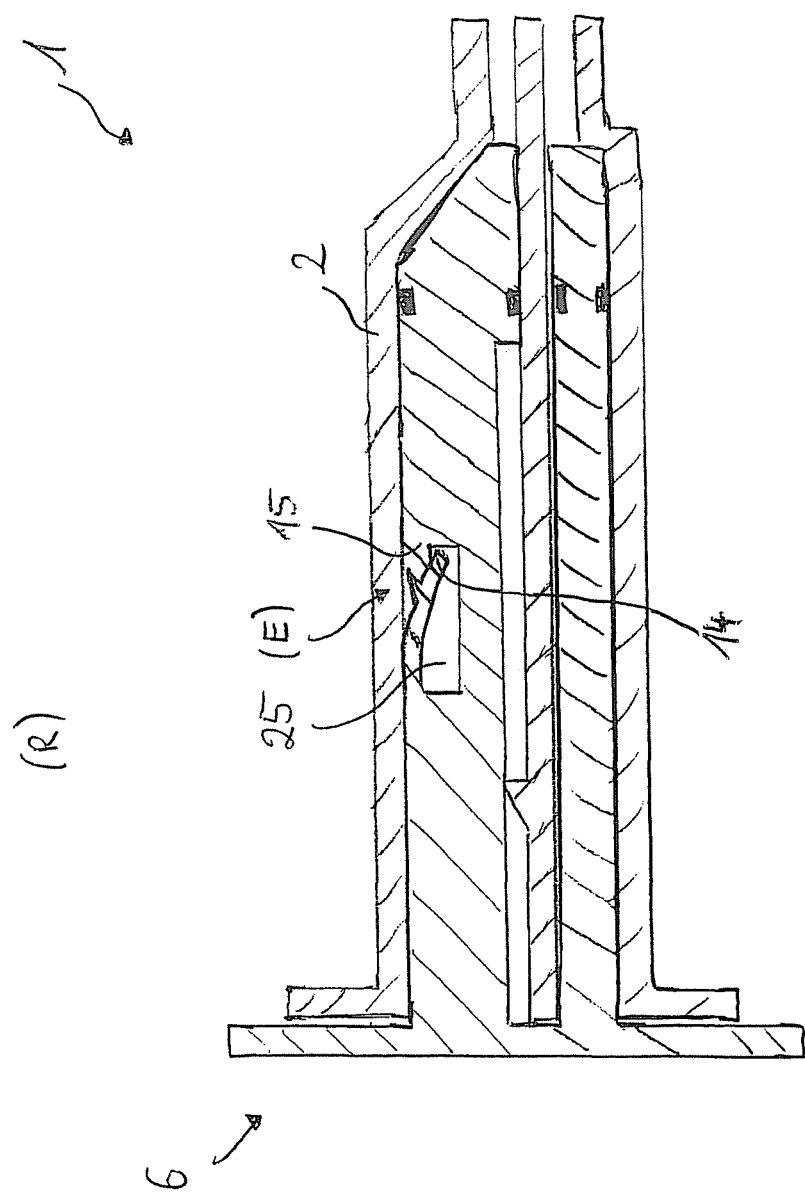
FIG. 4 shows the dispensing device of FIG. 1 in the simultaneous releasing position and engagement position.

By exerting an inward radial force F on the retaining arm 13, the latter is pushed radially inwardly and further into the cavity 25. As a result, the tip 14 snaps behind the retaining surface 15, whereby an engagement position E is obtained between the tip 14 and the retaining surface 15 (cp. FIG. 4). This force F may be applied with a single finger, which significantly facilitates the operation.

Once the engagement position E is obtained, the tooth 12 cannot contact the rear surface 9 of the main body 2 and the locking position cannot be obtained anymore. Therefore, even when the operator's finger is removed and, thereby, the force F is also removed, the engagement position is maintained, which further simplifies the operation.

In the engagement position E thus obtained, the plunger unit 6 is movable again in both directions (with the limitation induced by the first stopping surface 27 and the second stopping surface 28), so that the releasing position R is obtained again and maintained. In this releasing position R, the plunger unit 6 may be re-inserted into the main body 2 again, so that the state shown in FIG. 4 can be obtained. In this state depicted in FIG. 4, the tooth 12 is not in contact with the inner surface of the first chamber 5.

Concludingly, in the engagement position E, the tooth 12 forming the locking means and the rear surface 9 forming the counter-locking means cannot be brought into the locking position L, since the tip 14 of the retaining arm 13 forming the catching means and the retaining surface 15 forming the counter-catching means are engaged with each other.

Figure 5A:
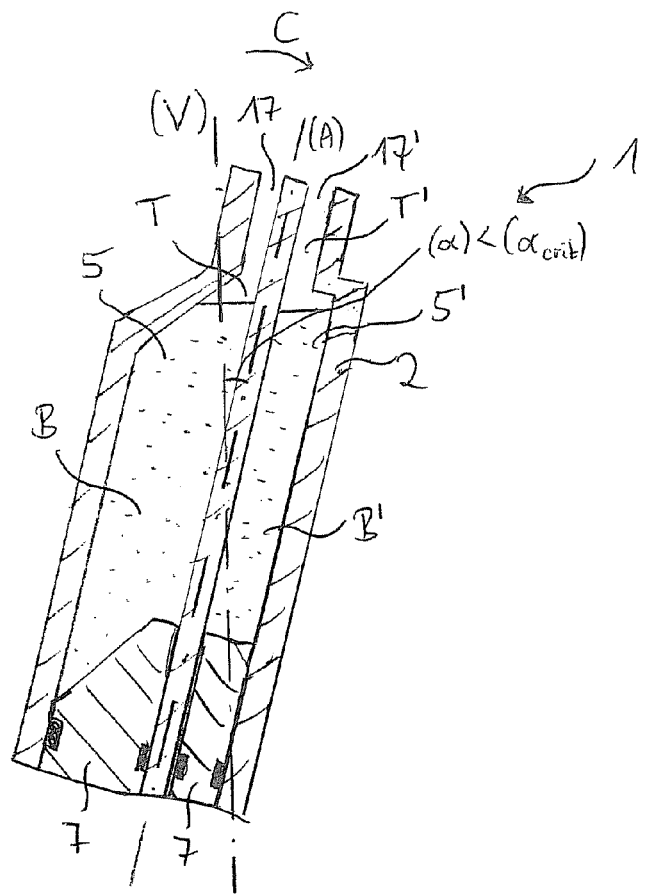
FIGS. 5a to 5c show a portion of the dispensing device of FIG. 1 at different tilting angles with filled-in fluids and air entrapments.
Figure 5B:
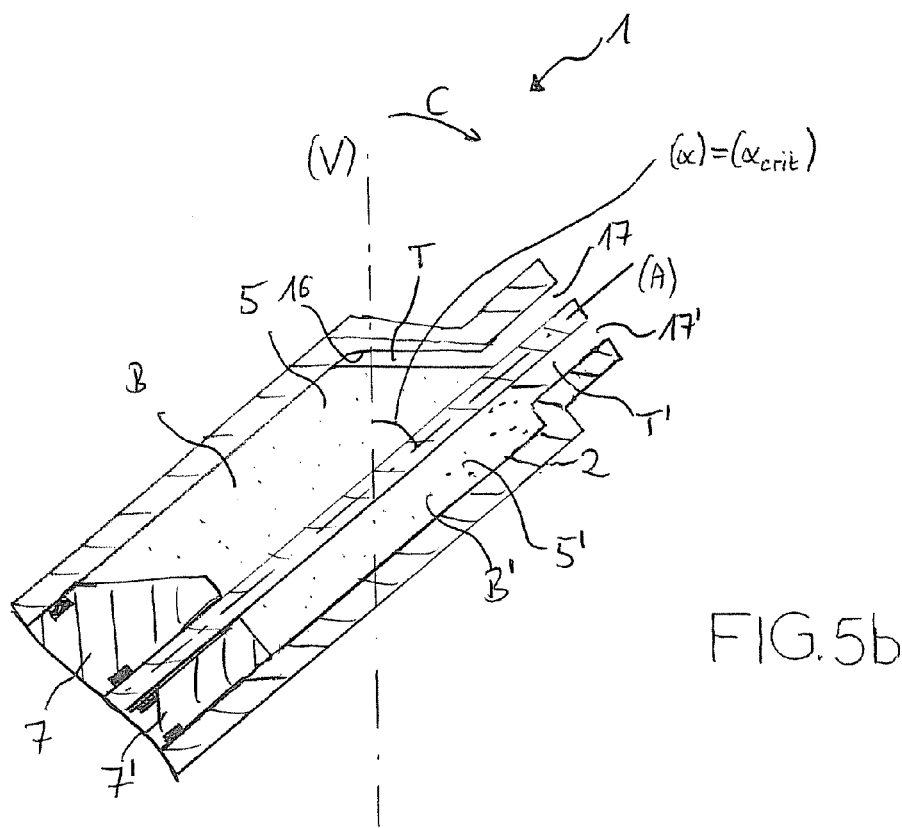
Figure 5C:
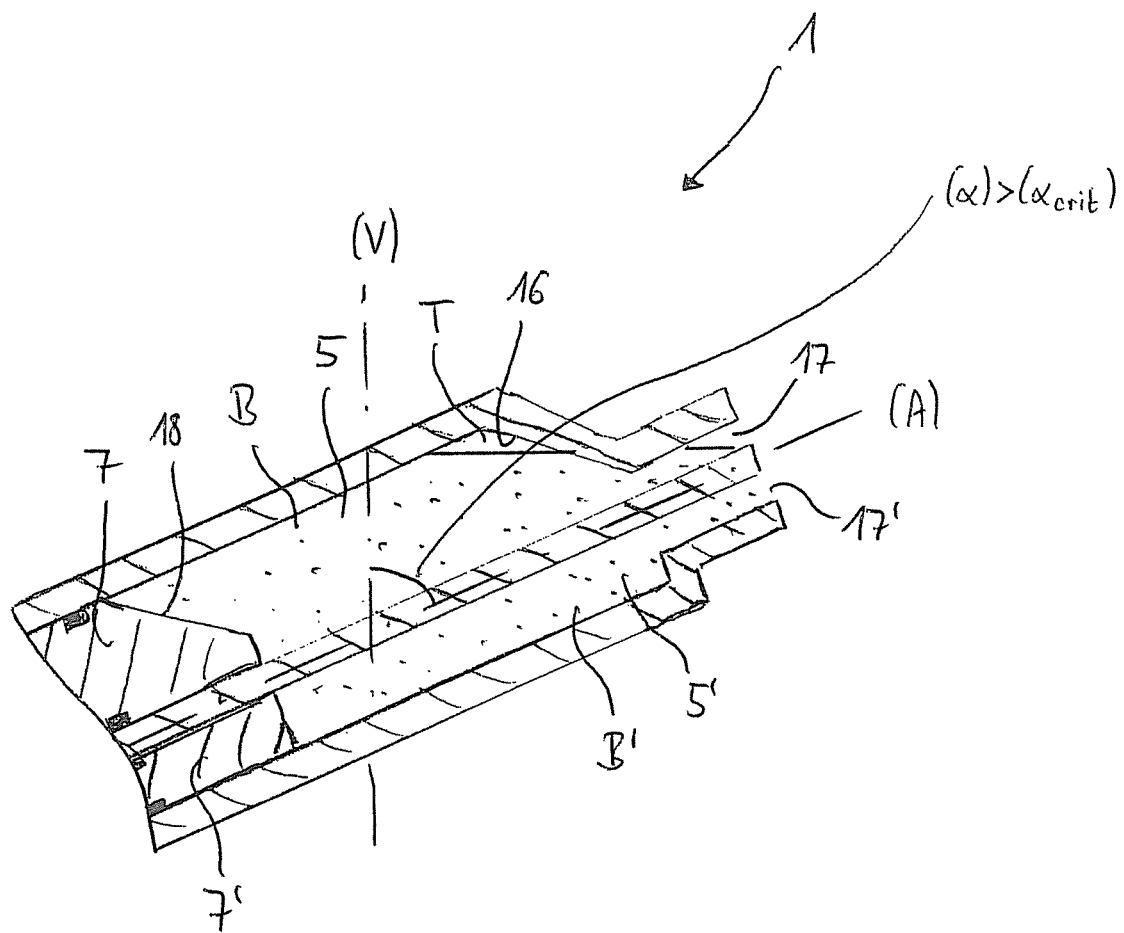

As shown in FIGS. 1 through 4 and also in FIGS. 5a through 5c, the end surface 16 of the first chamber 5 is inclined from a plane which is perpendicular to the longitudinal axis A of the device 1. Hence, the cross-section of the first chamber 5 is reduced in the direction of the opening 17, i. e. in the direction of the front end 3. The end surface 16' of the second chamber 5' is perpendicular to the longitudinal axis A. Both end surfaces 16,16' are essentially planar and are adjacent to the openings 17,17'. The openings 17,17' are arranged adjacent to one another, so that the distance between the openings 17,17' is smaller than one-half of the sum of the inner dimensions of the chambers 5,5' in the drawing plane. In particular embodiments, the distance between the centers of the openings may be 3.2 mm or 4 mm. This allows the ejection of fluids at positions which are close to each other and can therefore facilitate an optional subsequent mixing of the fluids, in particular by a relatively small mixing assembly.

The tip surfaces 18 of the pistons 7,7' are complementary to the end surfaces 16 of the respective chambers 5,5'. Therefore, prior to injecting fluids into the chambers 5,5', when the pistons 7,7' are completely inserted, there are essentially no air entrapments in the chambers 5,5'. Furthermore, during re-ejection of fluids through the openings 17,17' by re-inserting the pistons 7,7', essentially no fluid can remain in the chambers 5,5'.

Figure 6:
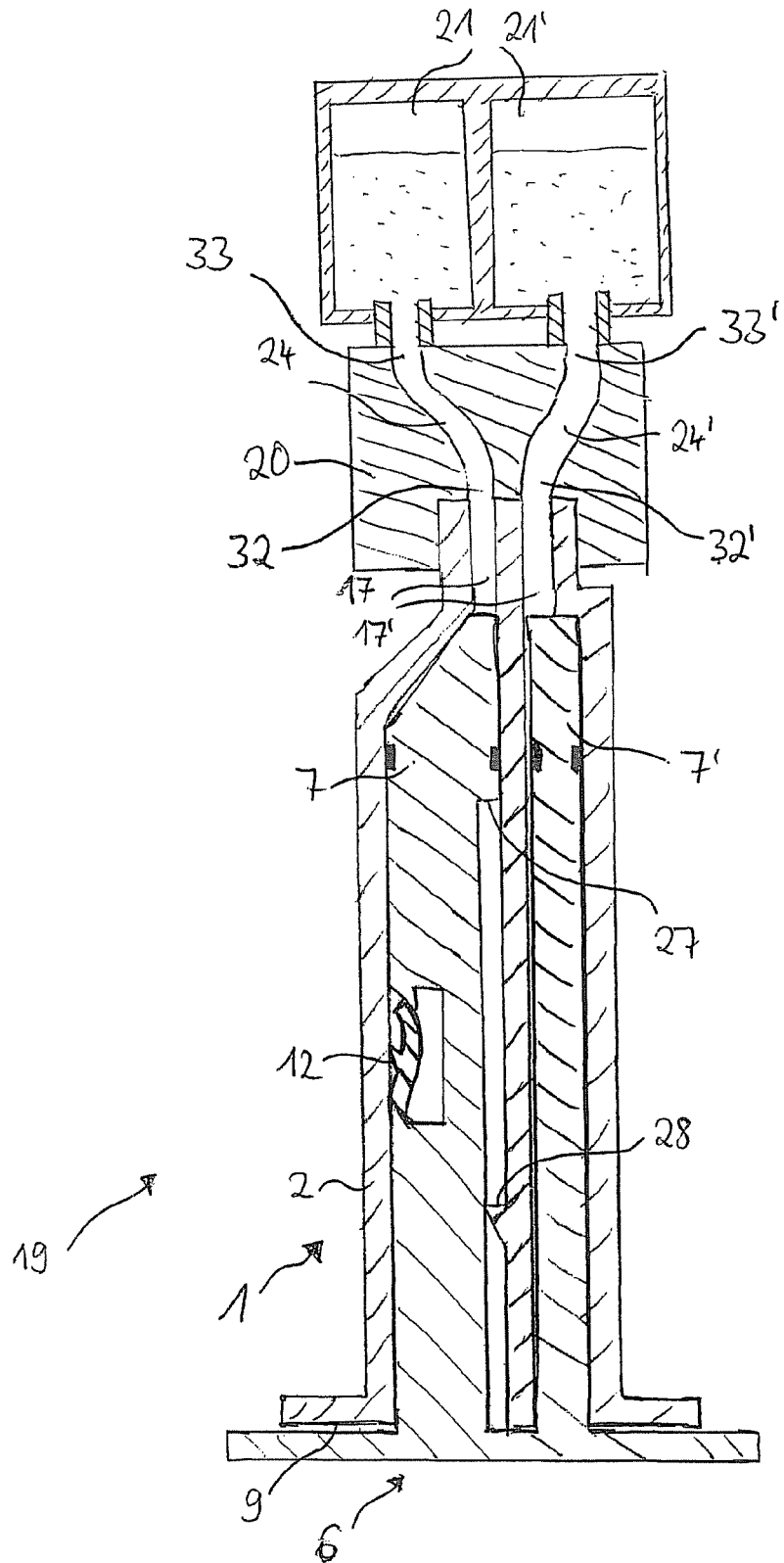
FIG. 6 shows a first kit according to the invention containing a dispensing device and a connecting adapter.

The purpose of the inclination of the end surface 16 is illustrated in FIGS. 5a to 5c. Each of the two chambers 5,5' contains a liquid B,B' and an air entrapment T,T'. The air entrapments T,T' may originate from air enclosures in a connecting adapter (cp. FIG. 6 and the description relating thereto). In FIG. 5a, the longitudinal axis A of the device 1 is tilted from the vertical axis V in the tilting direction C about a tilting axis by an angle α. The tilting axis is perpendicular to the drawing plane. In FIG. 5a, the tilting angle α does not exceed a critical tilting angle $\alpha_{crit}$, which is approximately 50°. For this tilting angle α shown in FIG. 5a, the air entrapments T,T' are adjacent to the openings 17,17' in the end surfaces 16,16'. Therefore, by inserting the plunger unit (of which only the pistons 7,7' are shown in FIGS. 5a and 5b), the air entrapments T,T' are ejected through the openings 17,17' simultaneously, leaving no dead volume of air entrapments.

In FIG. 5b, the longitudinal axis A is tilted from the vertical axis V in the tilting direction C by an angle α which is equal to the critical tilting angle $\alpha_{crit}$. For this tilting angle α, the surface of the fluid B in the first chamber 5 is parallel to the end surface 16 of this first chamber 5. Thus, this is the maximum tilting angle for which the air entrapment T is adjacent to the opening 17 and can therefore be ejected through the opening 17 by inserting the plunger unit 6.

Finally, FIG. 5c depicts a situation in which the tilting angle α exceeds the critical tilting angle $\alpha_{crit}$. With this tilting angle α, the air entrapment T in the first chamber 5' can only escape through the opening 17 when the piston 7 is completely inserted into the chamber 5, so that its tip surface 18 contacts the end surface 16. However, in this position, the entire fluid B has already been ejected through the opening 17.

The specific embodiment disclosed above exhibits catching means and counter-catching means as well as corresponding surfaces of the piston tips and chambers, along with the respective advantages described above. However, it is clear that both aspects are independent from one another and that the omission of one of the aspects does not impede the function and advantages of the other aspect. For example, the device may exhibit catching means and counter-catching means according to the invention but have chambers with plane end surfaces which are perpendicular to the longitudinal axis of the device.

FIG. 6 shows a kit 19 containing a dispensing device 1, a connecting adapter 20, and two fluid reservoirs 21,21'. For simplicity, only a part of the device is shown. The connecting adapter 20 contains two ducts 24,24', each of which connects one of the openings 17,17' of the device 1 with a respective fluid reservoir 21,21'. More explicitly, a first end of each duct 24,24' opens out into a respective device-facing opening 32,32', which is connectable or connected with a respective opening 17,17' of the device 1. Furthermore, a second end of each duct 24,24', opposite to the respective first end of the duct 24,24', opens out into a respective reservoir-facing opening 33,33' which is connectable or connected with a respective fluid reservoir 21,21'. The connecting adapter 20 thereby allows a simultaneous filling of the first chamber 5 and the second chamber 5'.

According to the method of the invention, the pistons 7,7' are retracted from the respective chambers 5,5', in particular by retracting the plunger unit 6 from the main body 2. During this retraction, air which was initially contained in the openings 17,17' and/or the connecting adapter 20 enters the chambers 5,5', which leads to air entrapments as shown in FIGS. 5a to 5c. By an optional reciprocating motion of the plunger unit 6, these air entrapments can be successively moved out of the chambers 5,5', through the openings 17,17' and the ducts 24,24' and into the reservoirs 21,21'.

When the fluid reservoirs 21,21' and the adapter 20 are sealed from the environment, this retraction has to be performed against a force induced by an under-pressure. The retraction is performed at least until the tooth 12 and the rear surface 9 of the main body 2 enter the locking position L shown in FIG. 2. In this locking position L, the plunger unit 6 cannot be pulled back into the main body 2 by the under-pressure.

Preferably, the plunger unit 6 is then further retracted from the main body 2 until the first stopping surface 27 and the second stopping surface 28 come into contact, as shown in FIG. 3. Thus, an excess of fluids B,B' is temporarily inserted into the chambers 5,5', which ensures that the openings 17,17' of the device 1 and the ducts 24,24' of the connecting adapter 20 are completely flooded with the respective fluids B,B'. The distance covered by the plunger unit 6 during this further retraction is pre-defined by the arrangement of the first stopping surface 27 and the second stopping surface 28.

According to a preferred embodiment, the first stopping surface 27 and the second stopping surface 28 are arranged such that the excess volume temporarily inserted in the chambers 5,5' is about 0.3 ml. This value has shown to be an advantageous compromise which guarantees that, on the one hand, the openings 17,17' and the ducts 24,24' are completely flooded with the respective fluids B,B' and, on the other hand, the under-pressure is not increased to such an extent that environmental air can enter the system through possible leaks.

In a next stop, the plunger unit 6 is released again, so that it moves back to the locking position due to the under-pressure which is present in the chambers 5,5'.

Subsequently, the openings 17,17' are disconnected from the respective fluid reservoirs 21,21' by removing the connecting adapter 20 from the openings 17,17'. Due to the remaining under-pressure in the fluid reservoirs 21,21', the fluids B,B' within the ducts 24,24' of the connecting adapter 20 will be sucked back into the respective fluid reservoirs 21,21'. Therefore, the fluids B,B' cannot drop out of the connecting adapter 20 during or after the process of disconnecting. This prevents an unintentional mixing and, possibly, a curing of the fluids B,B', which could lead to a clogging of the openings 17,17'.

In the next step (which is not illustrated), the tip 14 of the retaining arm 13 is pushed behind the retaining surface 15 by exerting a force on the retaining arm 13. This operation may be performed with a single finger, which simplifies the process. Thus, the engagement position E is obtained, in which the locking position is disabled, so that the plunger unit 6 is again movable in both directions, as was described above in relation to FIGS. 2 to 4. When the force is removed, the engagement position is maintained, so that a return to the locking position is further impeded. Since at this time, an under-pressure is not present in the chambers 5,5' anymore, the pistons 7,7' cannot be pulled back into the chambers 5,5' unintentionally.

In a next (optional) step, possible air entrapments which might still be contained in the chambers 5,5' are ejected, as was described above in relation to FIGS. 5a and 5b.

In a further (optional) step, a mixing assembly 22 and a spray assembly 23 are connected to the openings 17,17'. However, it is also conceivable that the openings 17,17' are already disconnected from the multiple connecting adapter 20 and the mixing assembly 22 and the spray 23 assembly are connected to the openings 17,17' before the disengagement position is obtained, i. e. before the tip 14 of the retaining arm 13 is pushed behind the retaining surface 15 by exerting a force on the retaining arm 13.

Figure 7:
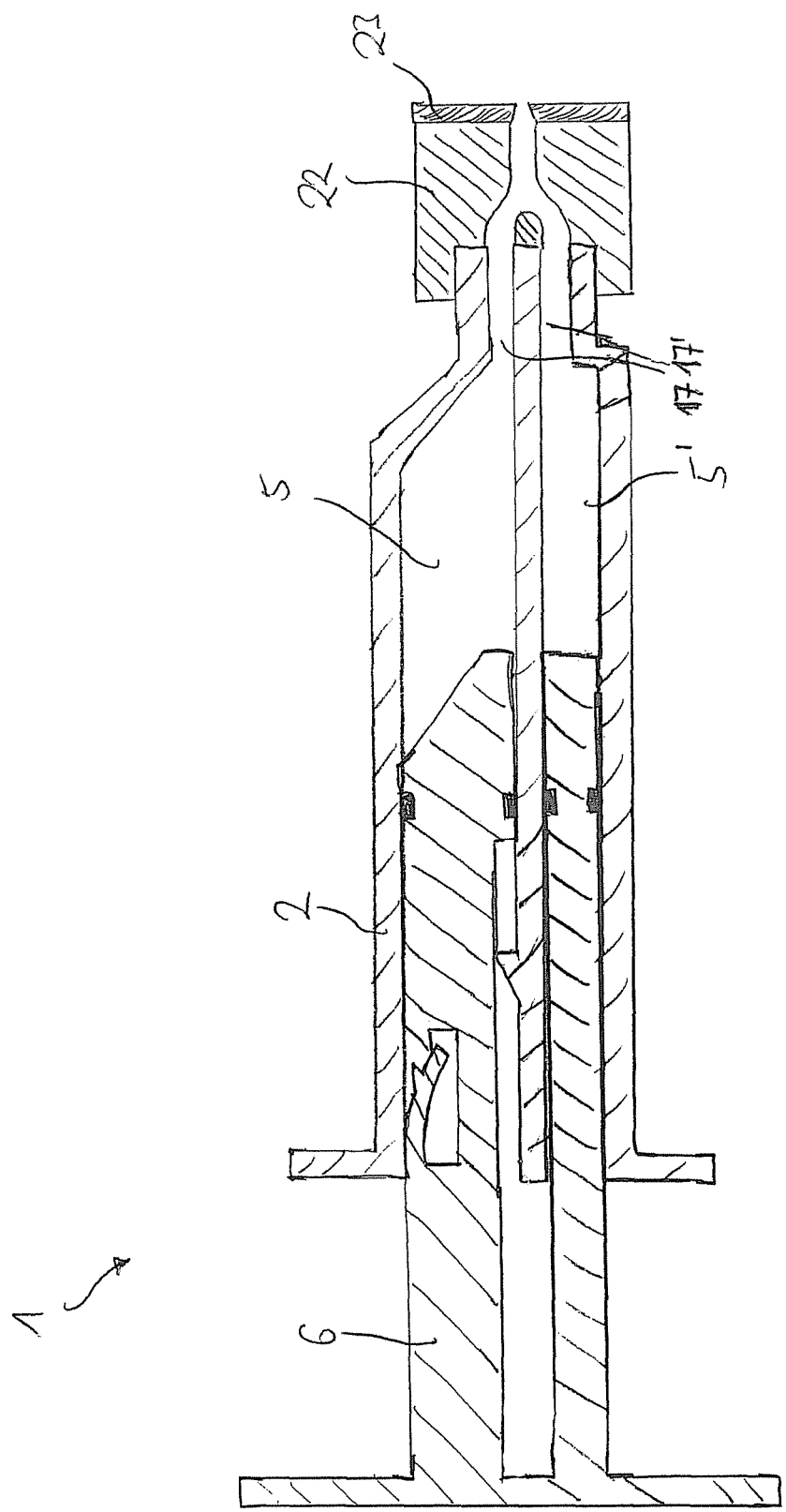
FIG. 7 show a first kit according to the invention containing a dispensing device, a mixing device, and a spraying device.

Finally, by at least partially inserting the pistons 7,7' into the chambers 5,5', the fluids are ejected through the openings 17,17' and (optionally) through the mixing assembly 22 and the spray assembly 23, as shown in FIG. 7.

FIGS. 8 through 14 show a second kit containing a second dispensing device 1 according to the invention, a connecting adapter 20, and two fluid reservoirs 21,21', wherein the reference numerals correspond to those used for the first embodiment depicted in FIGS. 1 through 7.

Figure 8:
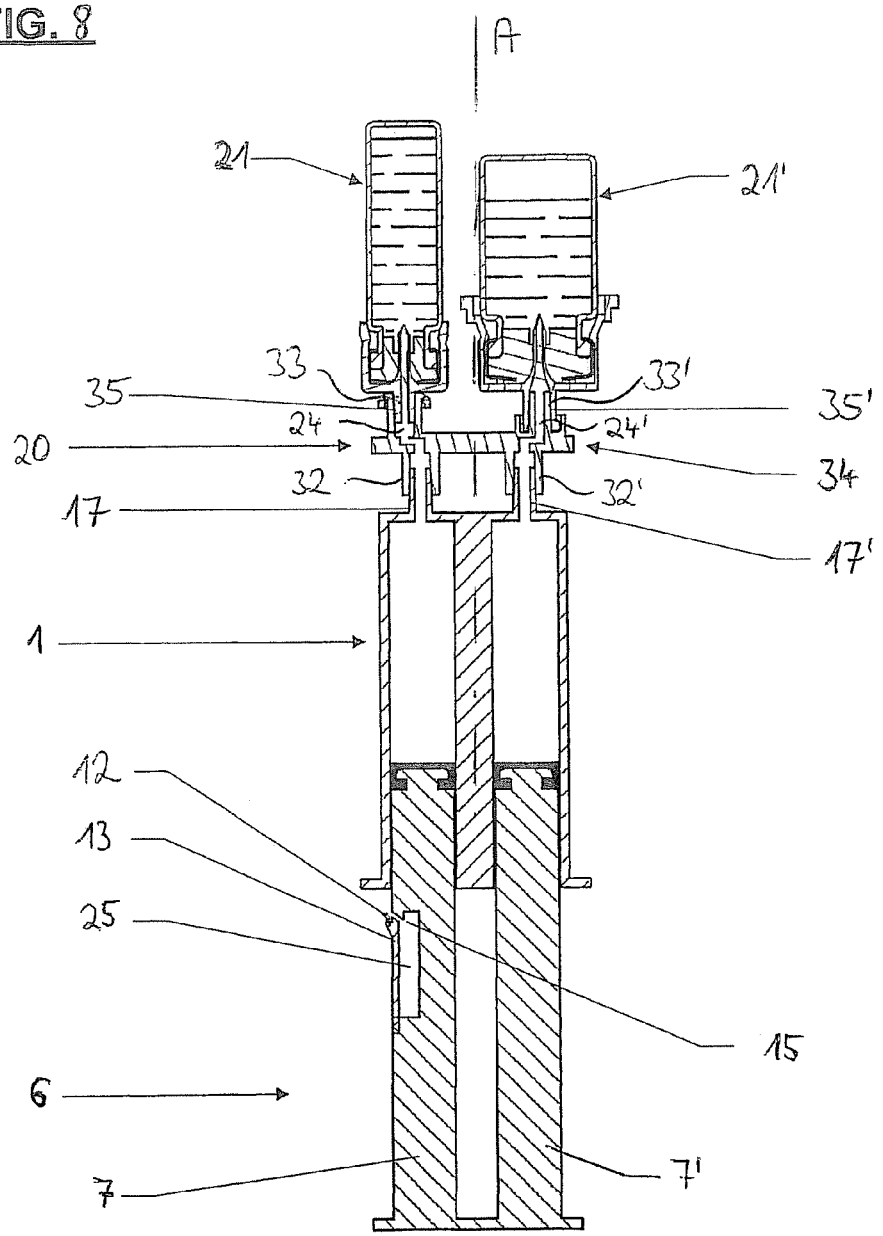
FIG. 8 shows a second kit according to the invention containing a second dispensing device in a simultaneous releasing position and disengagement position, a connecting adapter, and two fluid reservoirs.

As opposed to the first embodiment, the chambers 5,5' of the second embodiment shown in FIG. 8 have identical cross-sections. Moreover, the cross-sections of the chambers 5,5' are not reduced in the direction of the respective openings 17,17', and the end surfaces 16,16' of the chambers 5,5' as well as the tip surfaces 18,18' of the pistons 7,7' are perpendicular to the longitudinal axis A of the device. Furthermore, the dispensing device 1 contains no stopping means arranged such that a movement of the plunger unit is limited in the direction from the front end to the rear end of the device; i. e. the plunger unit 6 contains no first stopping surface, and none of the chambers 5,5' contains a second stopping surface, as it is the case for the embodiment shown in FIGS. 1 through 7. The openings 17,17' are conical.

The connecting adapter 20 contains two ducts 24,24', each of which connects one of the openings 17,17' of the device 1 with a respective connector 35,35' of a fluid reservoir 21,21'. More explicitly, a first end of each duct 24,24' opens out into a respective device-facing opening 32,32', which is connected with a respective opening 17,17' of the device 1. Furthermore, a second end of each duct 24,24', opposite to the respective first end of the duct 24,24', opens out into a respective reservoir-facing opening 33,33' which is connected with a respective fluid reservoir 21,21'. The connecting adapter 20 thereby allows a simultaneous filling of the first chamber 5 and the second chamber 5'.

Figure 9:
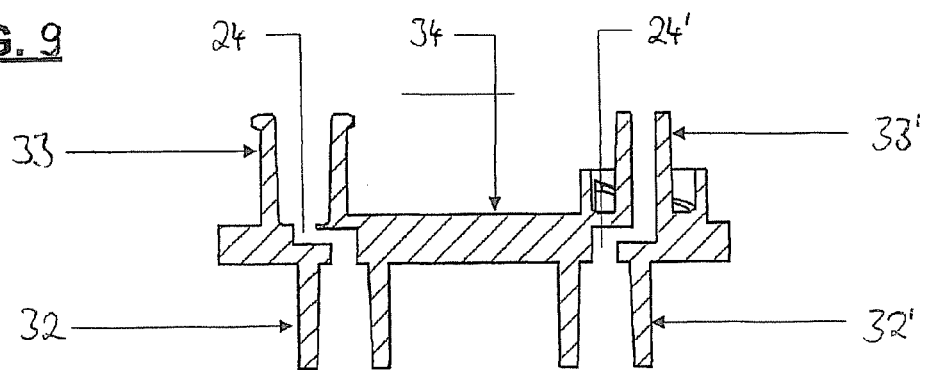
FIG. 9 show the connecting adapter of the kit shown in FIG. 8.
Figure 14:
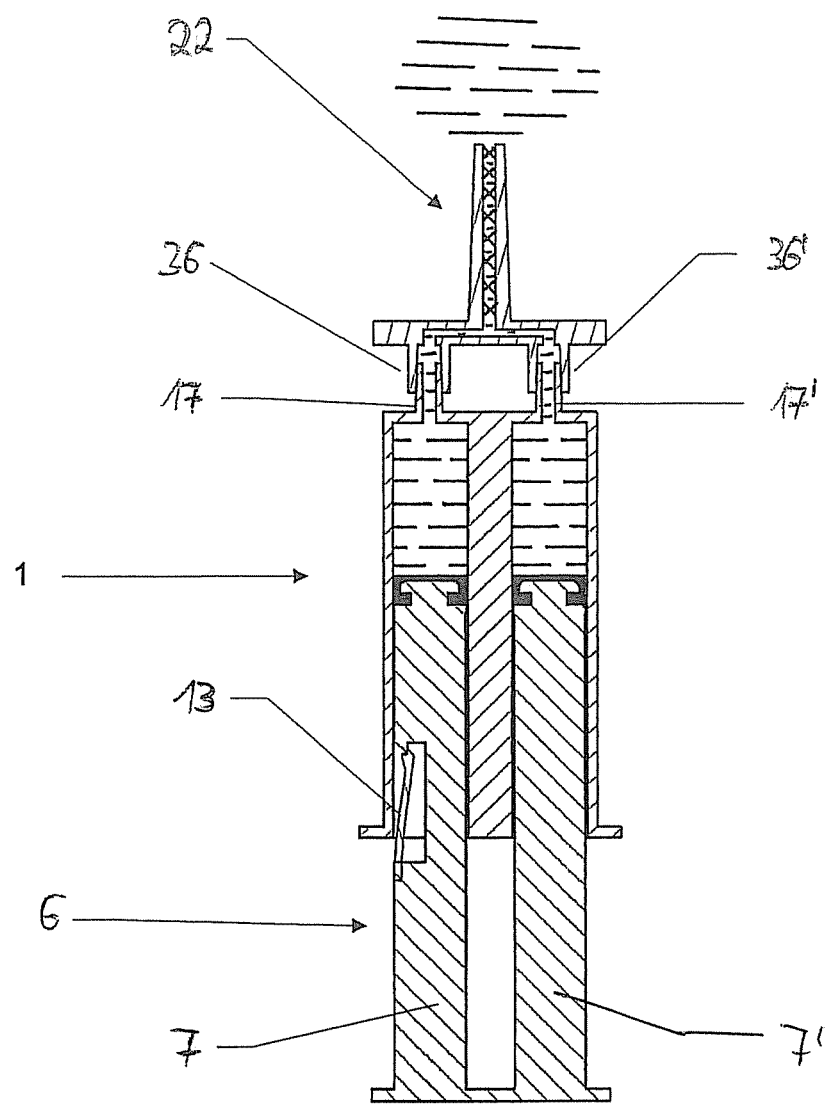
FIG. 14 shows the second dispensing device of FIG. 8 and a mixing device, wherein the dispensing device is in the simultaneous engagement position and releasing position and the plunger unit is inserted into the chambers.

A more detailed view of the connecting adapter 20 is provided in FIG. 9. It contains a disc-shaped main body 34. On one of the sides of the main body 34, two device-facing openings 32,32' are arranged for connection with the respective openings of the dispensing device. On the opposite side of the main body 34, two reservoir-facing openings 33,33' are arranged for connection with two respective reservoir connectors 35,35'. The conical device-facing opening 32 and the reservoir-facing opening 33 are connected by the duct 24, whereas the conical device-facing opening 32' and the reservoir-facing opening 33' are connected by the duct 24'. The reservoir-facing opening 33 is designed as a female Luer lock connector, whereas the reservoir-facing opening 33' is designed as a male Luer lock connector.

FIGS. 10 through 14 show the filling, adjusting, and ejecting of two liquid components. FIG. 10 depicts the original position in which the dispensing device 1 is connected to one side of the connecting adapter 20 and the two reservoirs 21,21' are connected to the other side of the connecting adapter 20. Both reservoirs 21,21' are filled, and in the original position, the pistons 7,7' are completely inserted in the chambers 5,5'. The retaining arm 13 is in the simultaneous releasing position R and disengagement position D, as shown in more detail in FIG. 10A.

In the situation shown in FIG. 11, the plungers 7,7' have been retracted so that the liquids have been sucked from the reservoirs 21,21' into the respective chambers 5,5' of the dispensing device 1. The retaining arm 13 has obtained the locking position L.

In order to adjust the amount of liquids contained in the chambers 5,5', the pistons 7,7' are re-inserted into the chambers 5,5' until the position shown in FIGS. 12 and 12A is obtained. In this position, the tooth 12 is in contact with the rear surface 12 of the dispensing device 1, thereby preventing a further insertion of the pistons 7,7' into the chambers 5,5'. As evident from FIG. 12, the air as well as a portion of the liquids has been re-introduced into the respective reservoirs 21,21', so that the chambers 5,5' are completely filled with the liquids and contain no air entrapments.

Prior to ejection, the two reservoirs 21,21' and the connecting adapter 20 are removed from the dispensing device 1, and a mixing assembly 22 is connected to the openings 17,17', as shown in FIG. 13. The mixing assembly 22 contains two mixer inlets 36,36', the conicity of which is adapted to that of the openings 17,17'. By exerting an inward radial force onto the retaining arm 13, the tip 14 of the retaining arm 13 snaps behind the retaining surface 15, as depicted in FIG. 13A. Thus, the retaining 13 has obtained the simultaneous engagement position E and releasing position R. In this position the pistons 7,7' can be further inserted into the chambers 5,5', so that the liquids are ejected (see FIG. 14).

The invention claimed is:

1. A dispensing device comprising
at least one chamber for receiving a fluid,
a plunger unit comprising at least one piston, each piston being arranged slidingly in one of the chambers,
locking means and counter-locking means, wherein the locking means and the counter-locking means can be brought into a locking position in which a movement of the plunger unit in one or both directions is substantially prevented,
catching means and counter-catching means which can be brought into an engagement position in which the locking means and the counter-locking means cannot be brought into the locking position and which can be brought into a disengagement position in which the locking means and the counter-locking means can be brought into the locking position,
wherein
(i) when the catching means and the counter-catching means are in the disengagement position and the locking means and the counter-locking means are in a releasing position in which a movement of the plunger unit is possible in both directions, the locking means and/or the counter-locking means are resiliently supported by a tensioned supporting element,
(ii) when the catching means and the counter-catching means are in the disengagement position and the locking means and the counter-locking means are in the locking position, the supporting element is less tensioned than in the releasing position,
and wherein
in the disengagement position the locking position is obtainable from the releasing position by a release of tension of the supporting element, and wherein this release of tension occurs automatically during retraction of the plunger unit.

2. The device according to claim 1, wherein
the device has a front end and a rear end, between which ends the at least one chamber extends,
in the locking position, a movement of the plunger unit in the direction from the rear end to the front end is substantially prevented.

3. The device according to claim 1, further comprising
stopping means which are arranged such that
a movement of the plunger unit is limited in the direction from the front end to the rear end of the device; and
when the locking means and the counter-locking means are in the locking position, the plunger unit is movable in the direction from the front end to the rear end by a predefined distance.

4. The device according to claim 1, wherein
the locking means comprise at least one radial protrusion.

5. The device according to claim 1, wherein the plunger unit comprises the catching means and the counter-catching means.

6. The device according to claim 5, wherein the plunger unit comprises
at least one retaining arm containing a tip forming the catching means and
a retaining surface forming the counter-catching means.

7. The device according to claim 6, wherein the retaining arm forms the supporting element.

8. The device according to claim 1, wherein the plunger unit comprises the locking means.

9. The device according to claim 1, wherein when the locking means and the counter-locking means are in the releasing position, the catching means and the counter-catching means are in the disengagement position.

10. The device according to claim 1, comprising
at least two chambers for receiving a fluid,
wherein the plunger unit comprises at least two pistons, wherein
each chamber has an end surface having an opening,
at least one of the chambers is designed such that
its cross-section is reduced in the direction of the respective opening and
when the device is tilted in a tilting direction by a tilting angle, not exceeding a critical tilting angle, all chambers have essentially no dead volume,
the openings are arranged adjacent to one another, wherein
a tip surface of at least one piston is essentially complementary to the end surface of the respective chamber.

11. The device according to claim 10, wherein the at least one surface is essentially planar and inclined by an angle with respect to a plane which is perpendicular to a longitudinal axis of the device.

12. The device according to claim 1, further comprising a component selected from the group consisting of
a multiple connecting adapter for directly or indirectly connecting openings of each of the chambers with a respective fluid reservoir simultaneously;
a mixing assembly for mixing fluids to be ejected from the chambers;
a spray assembly for spraying fluids to be ejected from the chambers; and
combinations thereof.

13. A method of operating a device according to claim 1, wherein the method comprises the following steps:
i) providing at least one fluid reservoir, wherein at least one of the fluid reservoirs comprises a fluid;
ii) directly or indirectly connecting openings of each chamber of the device with a respective fluid reservoir;
iii) at least partially retracting the piston or pistons of the device from the chamber or chambers;
iv) allowing the locking means and the counter-locking means to obtain the locking position;
v) disconnecting the openings from the respective fluid reservoirs;
vi) bringing the catching means and the counter-catching means into the disengagement position;
vii) at least partially inserting the pistons into the chambers, thereby ejecting the fluids.

* * * * *